United States Patent [19]

Iba et al.

[11] Patent Number: 4,509,838
[45] Date of Patent: Apr. 9, 1985

[54] OPTICAL SYSTEM FOR RETINAL CAMERAS

[75] Inventors: Youich Iba; Ken-ichi Nakahashi; Masaki Matsubara, all of Hachiouji, Japan

[73] Assignee: Olympus Optical Co., Ltd., Tokyo, Japan

[21] Appl. No.: 575,580

[22] Filed: Jan. 31, 1984

Related U.S. Application Data

[63] Continuation-in-part of Ser. No. 260,398, May 4, 1981, abandoned.

[30] Foreign Application Priority Data

May 8, 1980 [JP] Japan .................................. 55-59992

[51] Int. Cl.³ .......................... G03B 29/00; G03B 9/08
[52] U.S. Cl. ...................................... 354/62; 351/206

[58] Field of Search .................. 354/62, 79; 351/6, 7, 351/13–17, 206

[56] References Cited

U.S. PATENT DOCUMENTS

| 3,089,398 | 5/1963 | Wilms | 351/7 |
| 3,217,622 | 11/1965 | Kiyono | 354/62 X |
| 3,778,135 | 12/1973 | Dianetti | 351/13 |
| 3,915,564 | 10/1975 | Urban | 354/62 X |

Primary Examiner—Donald A. Griffin
Attorney, Agent, or Firm—Cushman, Darby & Cushman

[57] ABSTRACT

An optical system for retinal cameras wherein the distance between an eye to be inspected and an inspector is made short to improve the operatability and to make it easy to handle the eye to be inspected.

36 Claims, 21 Drawing Figures

OPTICAL SYSTEM FOR RETINAL CAMERAS

CROSS REFERENCES TO RELATED APPLICATIONS

This application is a continuation-in-part of application Ser. No. 260,398, filed May 4, 1981 and now abandoned.

BACKGROUND OF THE INVENTION (a) Field of the Invention

This invention relates to small retinal cameras and more particularly to improvements in an optical system for small retinal cameras.

(b) Description of the Prior Art

FIG. 1 shows a conventional example of an optical system for retinal cameras. In the drawing reference numeral 1 denotes an eye to be inspected, 2 denotes an objective, 3 denotes a mirror having an aperture in the center, 4 denotes a relay lens, 5 denotes a film surface, 6 denotes a reflector for switching a light path, 7 denotes an observing optical system consisting of a reflector 7a, reticle 7b and eyepiece 7c, 8 denotes an eye of an inspector and 10 denotes an illuminating optical system consisting of a light source 10a, collector lens 10b, ring slit 10c and projecting lens 10d. In such optical system, a light from the light source 10a of the illuminating optical system 10 is projected onto the ring slit 10c through the collector lens 10b. The illuminating light having passed through the ring slit 10c is reflected by the mirror 3 and is projected onto the eye 1 to be inspected through the objective 2 and, as a result, the eye 1 to be inspected is annularly illuminated. The light reflected from the thus illuminated retina passes through the objective 2 and further through the central aperture of the mirror 3 and is focused on the film surface 5 by the relay lens 4. On the other hand, when the reflector 6 is present within the light path as illustrated, the light from the retina will be reflected by the reflector 6 and will be focused on the reticle 7b and therefore the retina can be directly observed through the eyepiece 7c.

As obvious from the above described explanation, in the conventional optical system for retinal cameras, as the respective optical elements from the objective 2 to the film surface 5 are arranged on a straight line, the distance between the eye 1 to be inspected and the eye 8 of the inspector is considerably long and the person to be inspected and the inspector will have to be positioned in a separated manner. As a result, it is difficult for the inspector not only to operate the camera but also to handle the eye to be inspected.

SUMMARY OF THE INVENTION

A primary object of the present invention is to provide an optical system for retinal cameras wherein the distance between an eye to be inspected and an eye of an inspector is made short to improve the operatability and to make it easy to handle the eye to be inspected.

According to the present invention, this object is attained by arranging between an objective and a relay lens at least two reflectors which bend a light path from the objective and then direct it to the relay lens.

Another object of the present invention is to provide an optical system for retinal cameras wherein, while the distance between an eye to be inspected and an eye of an inspector is made short, a space for a focusing optical system can be taken to be large and such auxiliary optical system as of a variable power lens can be easily set.

A further object of the present invention is to provide an optical system for retinal cameras wherein the positions of eyes of a person to be inspected and an inspector can be kept proper and such other optical systems as an automatically focusing optical system and an image intensifier can be easily arranged.

Another further object of the present invention is to provide an optical system for retinal cameras wherein an image of a retina can be respectively photographed on two kinds of films set in advance in the camera by only a simple switching operation.

These and other objects of the present invention will become more apparent during the course of the following detailed description and appended claims.

DESCRIPTION OF THE PREFERRED EMBODIMENTS

Figure 1:
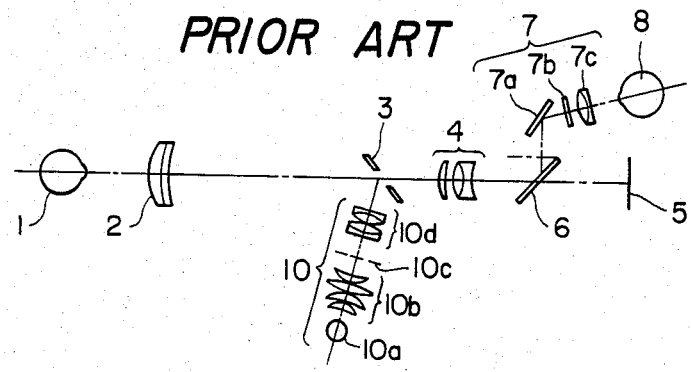
FIG. 1 is a view showing a conventional optical system for retinal cameras.
Figure 2:
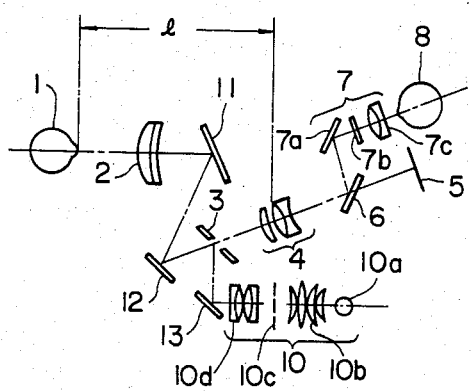
FIG. 2 is a view showing a first embodiment of an optical system for retinal cameras according to the present invention.

The contents of the optical system of the present invention shall be explained with reference to the illustrated embodiments. In the respective embodiments, the same reference numerals are attached to substantially the same elements. Shown in FIG. 2 is the first embodiment. In this drawing, reference numerals 11 and 12 denote reflectors for bending the light path provided between objective 2 and the mirror 3 having the central aperture in the conventional optical system for retinal cameras shown in FIG. 1. The other optical systems have only variations made by bending the light path by providing the reflectors 11 and 12 and are substantially the same as the conventional example. Therefore, the same reference numerals are attached to the same optical elements as in FIG. 1 and detailed explanations shall be omitted. By the way, the reflector 13 may not be used but had better be used to compact the retinal camera because, in case it is not used, the illuminating optical system will extend downward. According to this embodiment, by bending the light path, the distance from the eye 1 to be inspected to the relay lens 4 is reduced to be much shorter than in the optical system in FIG. 1. Therefore, the distance between the eye to be inspected and the inspector can be made so short that it is very easy to operate the camera and to handle the eye to be inspected. In the conventional retinal camera, if a variable power optical system for varying the photographing magnification or a light measuring optical system for the automatic stroboflash is to be inserted, the light path length will become larger, the distance between the eye to be inspected and the eye of the inspector will become larger and the operability will become very low. However, in the optical system of the present invention shown in FIG. 2, such defects can be eliminated.

Figure 3:
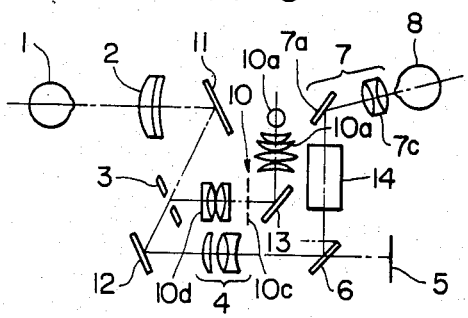
FIG. 3 is a view showing a second embodiment of an optical system for retinal cameras according to the present invention.

In FIG. 3 showing the second embodiment of the present invention, light paths of a photographing optical system and observing optical system are so arranged as to be U-shaped by using reflectors 11 and 12, a reflector 3 is arranged between the reflectors 11 and 12 and an illuminating optical system 10 is set within a space enclosed with the light paths of the photographing optical system and observing optical system. In this embodiment, a dark tube or image multiplying tube 14 is arranged between a switching reflector 6 and a reflector 7a.

This is an example of a retinal camera wherein the pupil of an eye to be inspected is opened by dark adaptation by making the illuminating light feeble or using, for example, infrared rays but without using a mydriatic. An image is made bright to be a visible image of a sufficient light amount while it is transmitted from the lower side end surface to the upper side end surface of a dark tube or the like being used because the illuminating light can not be made bright. In such conventional retinal camera as is shown in FIG. 1, if a dark tube or the like being used is inserted between the switching reflector 6 and reflector 7a, the difference between the heights of the optical axis of the objective and optical axis of the eyepiece will become so large that the operability will become very low. However, in this embodiment, if the light paths of the photographing optical system and observing optical system are so arranged as to be U-shaped, the heights of the optical axes of both optical systems can be made the same and the operability of the camera can be made very high. In this embodiment, not only the dark tube but also any element can be inserted as required. Further, its setting place is not limited to be between the switching reflector 6 and reflector 7a but may be, for example, between the reflector 12 and switching reflector 6. In any case, if each reflector is positioned as shown in FIG. 3, an arrangement high in the operability will be able to be obtained.

Figure 4:
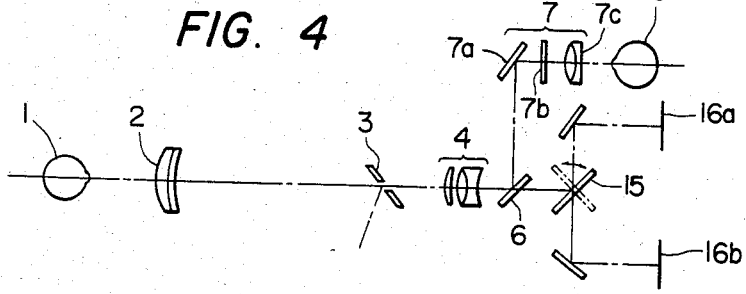
FIGS. 4 and 5 are views showing optical systems of double cameras each having two film cases.
Figure 5:
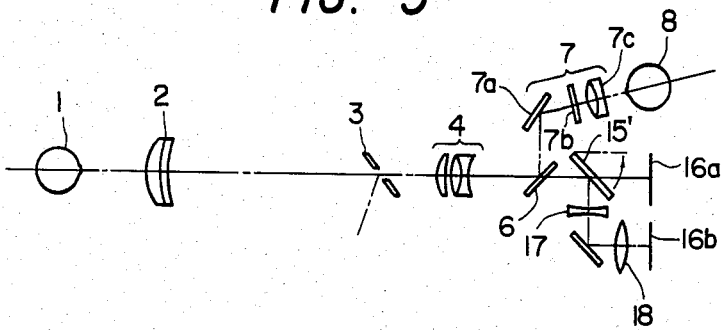

Usually, in a retinal camera, a color film is used for a general photographing and a monochromatic film is used for a fluorescent light photographing. A sole color film case and monochromatic film case are prepared to be interchanged with each other in each photographing. As a retinal photographing is carried out in the dark, the operation of interchanging the film cases is very difficult. In order to prevent this difficulty, it is preferable to set two film cases on a retinal camera so that two kinds of films can be respectively used by only a simple light path switching. For an optical system for switching these two film cases, such double camera to be so called (this kind of camera shall be called a double camera hereinafter) as is shown in FIG. 4 or 5 is considered. In the one shown in FIG. 4 of these optical systems, another switching reflector 15 is arranged just behind the switching reflector 6 and is rotated as indicated by the arrow to switch the solid line position and chain line position on each other. Thereby a color film surface 16a and monochromatic film surface 16b can be switched on each other in focus. In FIG. 5, a switching reflector 15' arranged behind the switching reflector 6 is made small in the movement as illustrated and auxiliary lenses 17 and 18 are used to adjust the focusing position produced thereby. In the optical system shown in FIG. 4 of the optical systems of such double cameras, the distance between the film surfaces 16a and 16b is long, the light path length from the photographing lens to the film surface is also long and therefore the reticle which must be in a position conjugate with the film surface must be taken to be long in the distance from the switching reflector 6. Therefore, the height difference between the optical axis of the objective and the optical axis of the eyepiece is large and the operability of the camera is low. In order to eliminate it, there are problems that auxiliary lenses are required and the optical system is complicated. In the example shown in FIG. 5, the distance between the films is not so large and the distance between the switching reflector and reticle need not be substantially changed. However, the exit pupil of the relay lens 4 is generally in a very far position, therefore the effective light pencil jetting out of the relay lens is considerably thick, the auxiliary lenses are of equal magnifications, enlarge only the light path and are arranged just before an image to be enlarged, therefore a concave lens of a strong power has to be adopted for the front group of the auxiliary lens system and the light pencil becomes thicker. Therefore, the succeeding optical system becomes large. Therefore, the aberration correction is also difficult and it is not preferable to use the auxiliary lens system.

Figure 6:
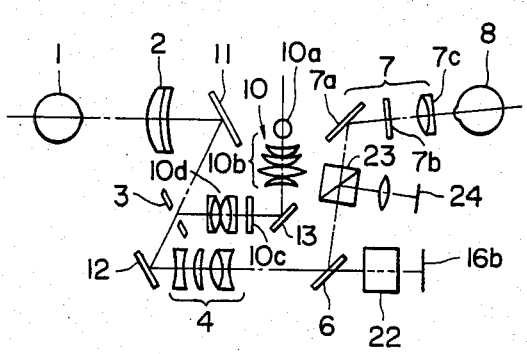
FIG. 6 is a view showing a third embodiment of an optical system for retinal cameras according to the present invention.
Figure 7:
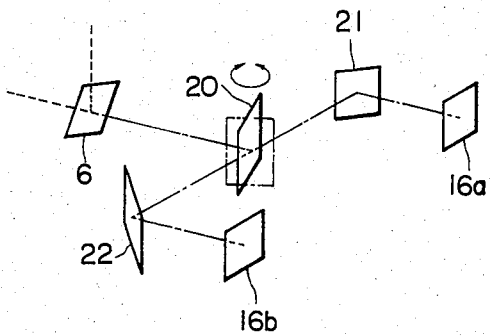
FIG. 7 is a view showing switching light paths to two film surfaces in the third embodiment.

In the third embodiment of the present invention shown in FIG. 6, a switching reflector 20 is arranged as shown in FIG. 7 behind the switching reflector 6 in the embodiment shown in FIG. 2 so as to switch the light pencil in the right and left directions, the light pencil on the right side is reflected by the reflector 21 and reaches the color film surface 16a and the light pencil on the left side is reflected by the reflector 22 and reaches the monochromatic film surface 16b. That is to say, the double camera shown in FIG. 4 or 5 is formed. In this case, the distances from the switching reflector 20 to both film surfaces 16a and 16b become long. Therefore, the distance to the reticle which is conjugate with the film surface must be also made long. However, when the distance between the reflectors 11 and 12 or the distance between the reflectors 6 and 7a (particularly the latter distance) is taken to be long, the height difference between the optical axis of the objective 2 and the optical axis of the eyepiece 7c and the distance between the eye 1 to be inspected and the inspector need not be made large. That is to say, a double camera can be formed without impairing the operatability at all and using any auxiliary lens system. By the way, in FIG. 6, reference numeral 23 denotes a beam splitter and 24 denotes a light receiving element for the automatic focusing and automatic stroboflashing. The optical system for this light receiving element can be simply set in the light path between the switching reflector 6 and reflector 7a.

Figure 8:
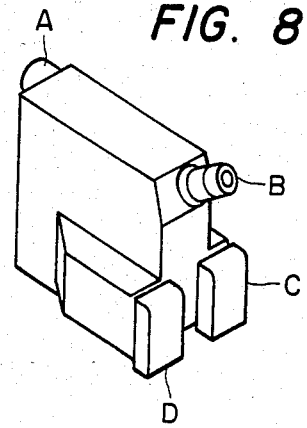
FIG. 8 is a perspective view of a double camera incorporating the optical system shown as the third embodiment of the present invention.

In FIG. 8 which is an appearance view of the double camera contained in the optical system of FIG. 6, symbol A denotes an objective part, B denotes an eyepiece part and C and D denote respective film cases.

Figure 9:
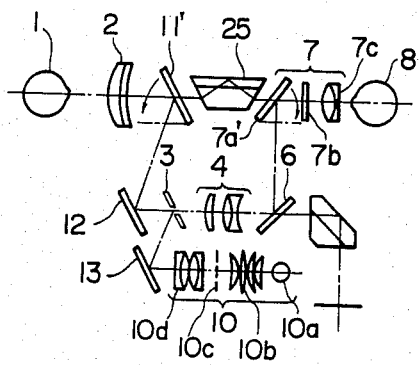
FIG. 9 is a view showing a fourth embodiment of an optical system for retinal cameras according to the present invention.

In the fourth embodiment of the present invention shown in FIG. 9, the front part of an eye to be inspected can be observed. That is to say, in observing the retina, it is necessary to accurately align the pupil of the eye to be inspected with the optical axis of the objective. Therefore, in observing the retina, it is necessary for the inspector to guide the eye to a correct position. In such case, it is convenient for the inspector to be able to observe the pupil of the inspected eye through the eyepiece. The fourth embodiment shown in FIG. 9 is provided with an optical system for this purpose. In this embodiment, the formations of the illuminating optical system and observing and photographing optical systems are substantially the same as of the optical system shown in FIG. 2 but are different from the embodiment in FIG. 2 in respect that the reflectors 11 and 7a of the optical system shown in FIG. 2 are formed as switching reflectors 11' and 7a' so that, when they are switched to the chain line positions, the light from the objective 2 will be able to be led directly to the eyepiece to observe the front part of the inspected eye. That is to say, in this embodiment, an image rotator 25 is arranged between the switching reflectors 11' and 7a' so that, when the reflectors 11' and 7a' leave the light path, the optical axes of the objective 2 and eyepiece 7c will align with each other through the image rotator 25. Further, the image of the pupil of the inspected eye by the objective is formed on the reticle 7b by adjusting the distance between the reflectors 11' and 7a'. This image can be observed through the eyepiece 7c and the eye to be inspected can be positioned. As the image rotator 25 is present here, the image can be observed as of the same shape as of the upright object. By the way, the image rotator 25 shown in FIG. 9 is a trapezoid Dach prism but may be of a lens and prism used to have the same function. Further, if the observation is not difficult even though the image is inverted, the image rotator need not be used.

Figure 10:
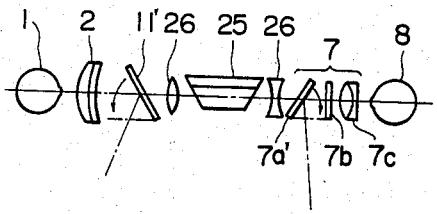
FIG. 10 is a view showing a modification of the optical system shown in FIG. 9.

In FIG. 10 showing an embodiment in which auxiliary lenses 26 are used in front and rear of the image rotator 25 in the embodiment in FIG. 9, thereby the image magnification and position of the pupil can be adjusted.

By the way, in the embodiments in FIGS. 9 and 10, one or both of the switching mirrors 11' and 7a' may be translucent.

Figure 11:
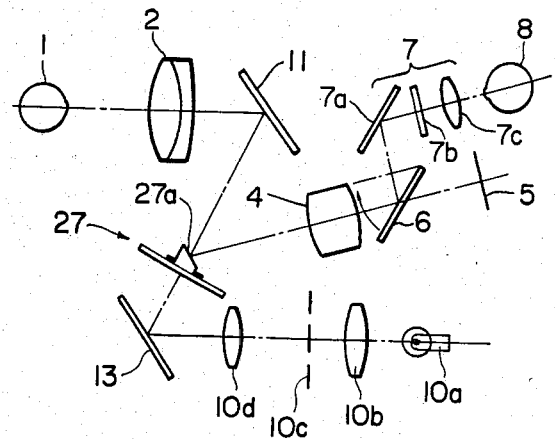
FIG. 11 is a view showing a fifth embodiment of an optical system for retinal cameras according to the present invention.
Figure 12:
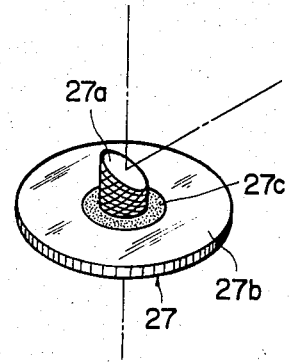
FIG. 12 is a perspective view of an optical element having a small reflecting surface and used in the fifth embodiment.

In the fifth embodiment of the present invention shown in FIG. 11, an optical element 27 having a small reflecting surface 27a is arranged in the position of and instead of the reflector 12 of the embodiment shown in FIG. 2, is of such structure as is shown in FIG. 12 and is provided with a projection having a small inclined reflecting surface 27a on an opaque part 27c in the center of a transparent part 27b made of such transparent material as glass. It is preferable that this opaque part 27c is larger than the small reflecting surface 27a. In this embodiment, a light from a light source 10a is focused on a ring slit 10c by a collector lens 10b, passes through the ring slit 10c, is then focused near the optical element 27, passes further through the transparent part 27b of the optical element 27 and is then projected on the cornea of the eye to be inspected by an objective 2. On the other hand, the light from the retina is once focused between the reflector 11 and optical element 27 by the objective 2 and is then reflected by the reflecting surface 27a of the optical element 27. Then, an observation or photographing is made in the same manner as in FIG. 2. In this embodiment, as described above, the image on the ring slit 10c is once focused near the optical element 27 and is then focused on the cornea surface. That is to say, as the image near the optical element 27 and the cornea surface are conjugated with each other, the light reflected by the cornea surface does not come back to the transparent part of the optical element 27, is not reflected by the small reflecting surface 27a and does not enter the photographing system. Therefore, as the retina image and the light reflected by the cornea surface are divided and selected from each other on the optical element 27, no flare will be produced in the retina image formed on the film surface 5 or reticle 7b. Further, as the small reflecting surface 27a acts the same as the mirror 3 having the aperture in the center, such mirror 3 is not required and therefore the formation is simple.

Figure 13:
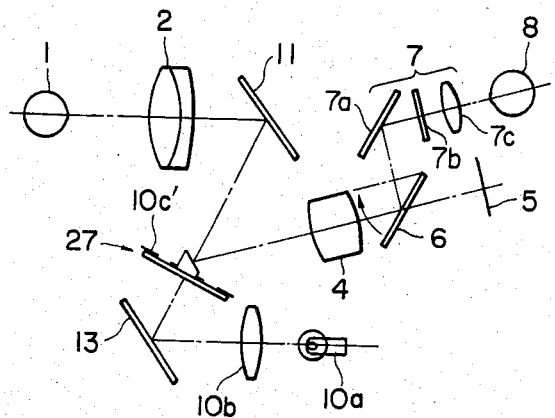
FIG. 13 is a view showing a sixth embodiment of an optical system for retinal cameras according to the present invention.

In the sixth embodiment of the present invention shown in FIG. 13, a ring slit 10c' is placed in the position of the optical element 27 so that, without using a projecting lens, the image of the light source 10a can be formed near the ring slit 10' and the image of the ring slit 10c' can be formed directly on the cornea of the eye to be inspected. The other points are substantially the same as in the fifth embodiment. As this sixth embodiment is formed as described above, no projecting lens is required and the formation can be made simpler and smaller. In this case, such optical element shown in FIG. 14 as an optical element in which the optical element 27 and ring slit 10c' are made integral may be used. That is to say, such transparent body 28 as a glass plate is painted in black or have shielding plates pasted on the central part 28c and peripheral part 28b so as to make shielding parts, is left transparent in the intermediate part between them so as to make an annular transparent part 28d to form a ring slit and has a projection having a small inclined reflecting surface 28a in the same manner as in FIG. 12 formed in the center. The central shielding part 28c of this optical element 28 has such role as is mentioned in the following. The image of the ring slit is formed on the cornea surface of the inspected eye by the objective but is likely to be collapsed by the aberration of the objective. Also, the position of the eye to be inspected is likely to be more or less displaced from the proper position perfectly conjugate with the ring slit. Further, the light reflected by the cornea surface is influenced by the aberration of the objective. From these facts, with only the small reflecting surface 28a, the retina image and detrimental reflected light can not be perfectly selected and divided from each other. In order to dissolve this problem, the central shielding part 28c is made larger than the small reflecting surface 28a to provide a cushion zone passing neither light between the part passing the light pencil of the retina image and the part passing the illuminating light pencil so that, even if the image collapses for the above described reasons, both light pencils will be able to be perfectly divided from each other to produce no flare.

Figure 14:
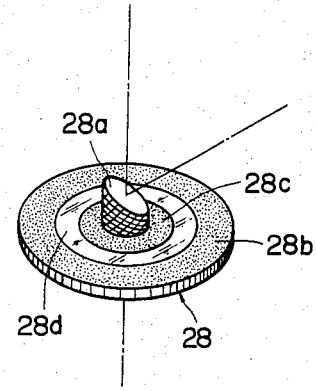
FIG. 14 is a perspective view of an optical element having a small reflecting surface and used in the sixth embodiment.

In the conventional example and the like, in order to have the same role as of the central shielding part of the optical element shown in FIG. 14 and the like, a diaphragm must be arranged near the central aperture of the mirror having the aperture in the center and is therefore inconvenient.

By the way, the optical elements shown in FIGS. 12 and 14 can be applied not only to the optical systems shown in FIGS. 11 and 13 but also to those of the second to fourth embodiments.

Figure 15:
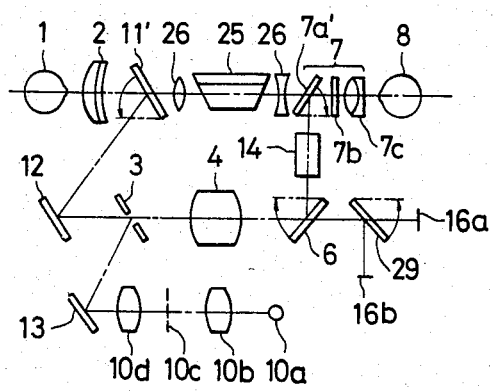
FIGS. 15 through 21 are views respectively showing a seventh through thirteenth embodiments of an optical system for retinal cameras according to the present invention.

FIG. 15 shows the seventh embodiment of the present invention. In this embodiment, a reflector 29 able to switch the light path is provided behind the reflector 6 and it is so formed that, as described in relation to FIGS. 4 and 5, the color film surface 16a and the monochromatic film surface 16b can be switched on each other in focus. Further, the dark tube 14 is provided between the reflector 6 and the switchable reflector 7a'. Still further, the image rotator 25 and the auxiliary lens 26 are provided between the switchable reflectors 11' and 7a'. This embodiment may be used in various modifications upon request by totally deleting the dark tube 14, the image rotator 25 and the auxiliary lens 26 or by selectively deleting these elements.

Figure 16:
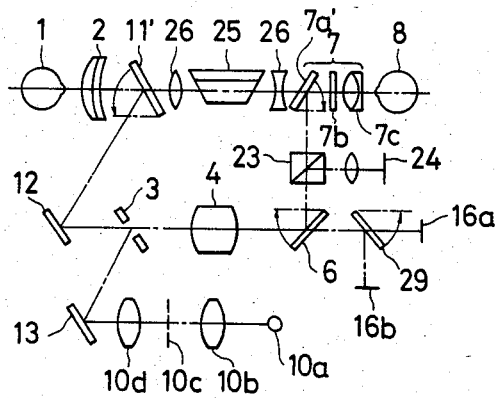

FIG. 16 shows the eighth embodiment of the present invention. This embodiment is different from the embodiment of FIG. 15 in that the beam splitter 23 is provided instead of the dark tube 14 and that the signals to effect the automatic focusing and automatic exposure controlling are able to be picked up by the light receiving element 24. Various changes and modifications are possible also in this embodiment. That is to say, it can be used totally deleting the beam splitter 23, the image rotator 25 and the auxiliary lens 26 or able to be used as what is so formed as to be selectively deleted of these respective elements.

Figure 17:
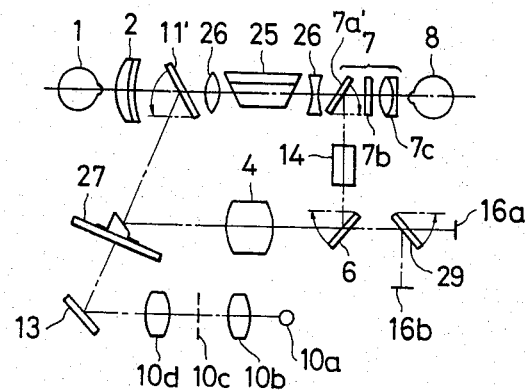

FIG. 17 shows the ninth embodiment of the present invention. This embodiment is different from the embodiment of FIG. 15 in that the mirror 3 and the reflector 12 are replaced by the optical element 27 of such formation as shown in FIG. 12. It is a matter of course that various changes and modifications such as described in relation to the embodiment of FIG. 15 are possible also in this embodiment.

Figure 18:
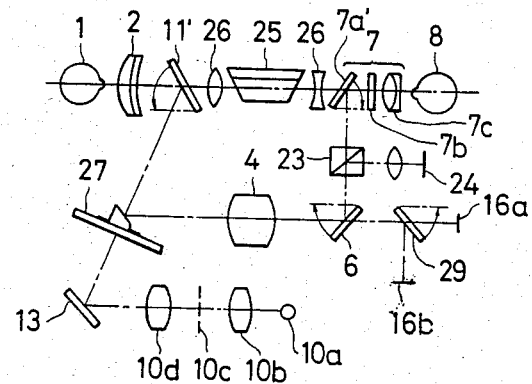

FIG. 18 shows the tenth embodiment of the present invention. This embodiment is different from the embodiment of FIG. 17 in that the dark tube 14 is replaced by the beam splitter 23 and that the signals to effect the automatic focusing and automatic exposure controlling are able to be picked up by the light receiving element 24. The aforementioned various changes and modifications are possible also in this embodiment.

Figure 19:
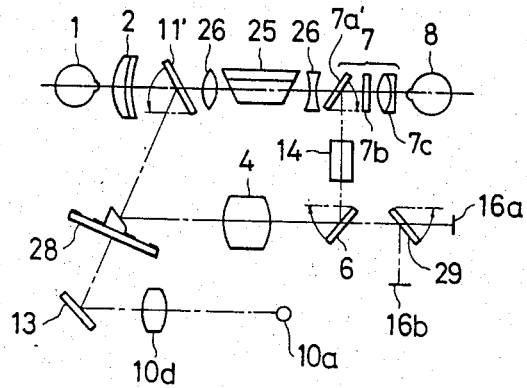

FIG. 19 shows the eleventh embodiment of the present invention. This embodiment is different from the embodiment of FIG. 17 in that the optical element 27 is replaced by the optical element 28 of such formation as shown in FIG. 14. The aforementioned changes and modifications are possible also in this embodiment.

Figure 20:
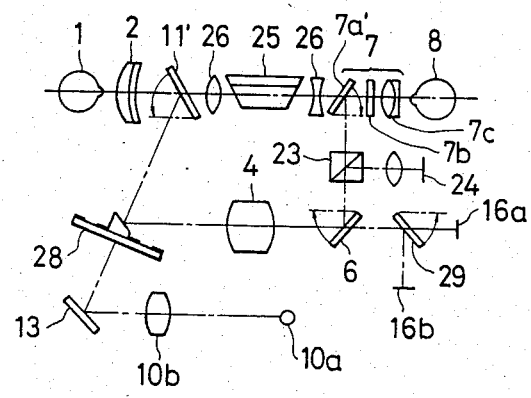

FIG. 20 shows the twelfth embodiment of the present invention. This embodiment is different from the embodiment of FIG. 18 in that the optical element 27 is replaced by the optical element 28 of such formation as shown in FIG. 14. The aforementioned various changes and modifications are possible also in this embodiment.

Figure 21:
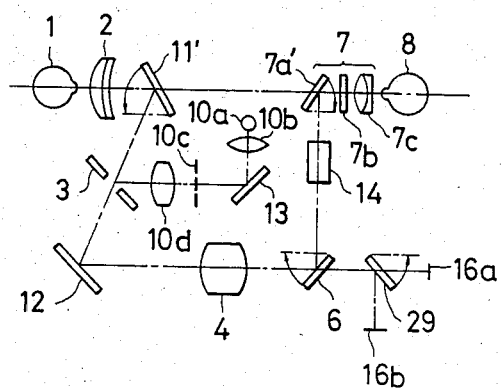

FIG. 21 shows the thirteenth embodiment of the present invention. This embodiment is different from the embodiment of FIG. 3 in that the reflectors 11 and 7a are replaced by the reflectors 11' and 7a' respectively able to switch the light path and that the pupil of the eye to be inspected is able to be observed by guiding the light from the objective lens 2 directly to the eyepiece 7. In this embodiment, the illumination optical system is arranged in the area enclosed by the light path bent by the reflectors 11' and 12 and the light path of the light reflected toward the eyepiece 7 by the reflector 6. Therefore, the retina camera can be formed still more compact.

We claim:

1. An optical system for retinal cameras comprising an objective for forming a retina image of an eye to be inspected, an illuminating optical system including therein a light source to illuminate the surface of the retina, a relay lens for leading to a film surface the retina image formed by said objective, a first reflector which can switch light paths and is arranged between said relay lens and the position of the retina image focused by said relay lens, an eyepiece arranged in the light path of the light reflected by said first reflector, characterized in that said optical system further comprises at least two light path bending second reflectors which are provided between said objective and relay lens, which bend the light path from the objective and then direct it to the relay lens, and an optical element arranged between said objective and relay lens and having one of said second reflectors and a transparent part by which the light from said illuminating optical system can be passed through around said one of said second reflectors.

2. An optical system for retinal cameras according to claim 1 wherein said optical element consists of a transparent plate having a shielding part in its center and a projection projecting out of said transparent plate and having a small reflecting surface.

3. An optical system for retinal cameras according to claim 2 further comprising a third reflector which can switch light paths and is arranged between said first reflector and the position of the retina image formed on said film surface by said relay lens so that a color film and monochromatic film can be arranged in the positions of the retina image by said relay lens in the respective light paths switched by said third reflector.

4. An optical system for retinal cameras according to claim 3 further comprising a light path bending fourth reflector which is provided between said first reflector and eyepiece, to bend the light path from said first reflector and then direct it to said eyepiece and a dark tube arranged between said first reflector, and fourth reflector.

5. An optical system for retinal cameras according to claim 3 further comprising a light path bending fourth reflector which is provided between said first reflector and eyepiece, to bend the light path from said first reflector and then direct it to said eyepiece, a beam splitter provided between said first and fourth reflectors and a light receiving element arranged in the light path of the light divided by said beam splitter to receive it and thereby to generate a signal for effecting at least one of automatic focusing and automatic exposure controlling.

6. An optical system for retinal cameras according to claim 2 wherein said optical system further comprises a third reflector which can switch light paths and is arranged between said first reflector and the position of the retina image formed on said film surface by said relay lens so that a color film and monochromatic film can be arranged in the positions of the retina image by said relay lens in the respective light paths switched by said third reflector, one reflector arranged in the position nearest to the objective of said reflectors is made a reflector which can switch light paths, a fourth reflector which can switch light paths is further arranaged between said first reflector and eyepiece so that, by switching the one of said second reflectors made a reflector which can switch light paths and said fourth reflector, the light having passed through the objective is led directly to the eyepiece and thereby the front part of the eye to be inspected can be observed.

7. An optical system for retinal cameras according to claim 6 wherein an image rotator is arranged in the light path directed directly to the eyepiece from the objective between the one of said second reflectors made a reflector which can switch light paths and said fourth reflector.

8. An optical system for retinal cameras according to claim 7 wherein auxiliary lenses for adjusting the magnification of the pupil and the position of the image are arranged near said image rotator.

9. An optical system for retinal cameras according to claim 6 further comprising a dark tube arranged between said first reflector and fourth reflector.

10. An optical system for retinal cameras according to claim 6 further comprising a beam splitter provided between said first and fourth reflectors and a light receiving element arranged in the light path of the light divided by said beam splitter to receive it and thereby to generate a signal for effecting at least one of automatic focusing and automatic exposure controlling.

11. An optical system for retinal cameras according to claim 2 further comprising a light path bending third reflector which is provided between said first reflector and eyepiece, to bend the light path from said first reflector and then direct it to said eyepiece.

12. An optical system for retinal cameras according to claim 1 wherein said optical element consists of a transparent plate shielded by leaving an annular transparent part and a projection projecting out of said transparent plate and having a small reflecting surface.

13. An optical system for retinal cameras according to claim 12 further comprising a third reflector which can switch light paths and is arranged between said first reflector and the position of the retina image formed on said film surface by said relay lens so that a color film and monochromatic film can be arranged in the positions of the retina image by said relay lens in the respective light paths switched by said third reflector.

14. An optical system for retinal cameras according to claim 13 further comprising a light path bending fourth reflector which is provided between said first reflector and eyepiece, to bend the light path from said first reflector and then direct it to said eyepiece and a dark tube arranged between said first reflector and fourth reflector.

15. An optical system for retinal cameras according to claim 13 further comprising a light path bending fourth reflector which is provided between said first reflector and eyepiece, to bend the light path from said first reflector and then direct it to said eyepiece, a beam splitter provided between said first and fourth reflectors and a light receiving element arranged in the light path of the light divided by said beam splitter to receive it and thereby to generate a signal for effecting at least one of automatic focusing and automatic exposure controlling.

16. An optical system for retinal cameras according to claim 12 wherein said optical system further comprises a third reflector which can switch light paths and is arranged between said first reflector and the position of the retina image formed on said film surface by said relay lens so that a color film and monochromatic film can be arranged in the positions of the retina image by said relay lens in the respective light paths switched by said third reflector, one reflector arranged in the position nearest to the objective of said second reflectors is made a reflector which can switch light paths, a fourth reflector which can switch light paths is further arranged between said first reflector and eyepiece so that, by switching the one of said second reflectors made a reflector which can switch light paths and said fourth reflector, the light having passed through the objective is led directly to the eyepiece and thereby the front part of the eye to be inspected can be observed.

17. An optical system for retinal cameras according to claim 16 wherein an image rotator is arranged in the light path directed directly to the eyepiece from the objective between the one of said reflectors made a reflector which can switch light paths and said fourth reflector.

18. An optical system for retinal cameras according to claim 17 wherein auxiliary lenses for adjusting the magnification of the pupil and the position of the image are arranged near said image rotator.

19. An optical system for retinal cameras according to claim 16 wherein auxiliary lenses for adjusting the magnification of the pupil and the position of the image are arranged near said image rotator.

20. An optical system for retinal cameras according to claim 12 further comprising a light path bending third reflector which is provided between said first reflector and eyepiece, to bend the light path from said first reflector and then direct it to said eyepiece.

21. An optical system for retinal cameras according to claim 1 further comprising a third reflector which can switch light paths and is arranged between said first reflector and the position of the retina image formed on said film surface by said relay lens so that a color film and monochromatic film can be arranged in the positions of the retina image by said relay lens in the respective light paths switched by said third reflector.

22. An optical system for retinal cameras according to claim 1 wherein said optical system further comprises a third reflector which can switch light paths and is arranged between said first reflector and the position of the retina image formed on said film surface by said relay lens so that a color film and monochromatic film can be arranged in the positions of the retina image by said relay lens in the respective light paths switched by said third reflector, and a fourth reflector which can switch light paths and is arranged between said first reflector and eyepiece, the one reflector arranged in the position nearest to the objective of said second reflectors being able to switch light paths, and whereby the light having passed through the objective is led directly to the eyepiece by switching said one of said second reflectors and said fourth reflector and thereby the front part of the eye to be inspected can be observed.

23. An optical system for retinal cameras according to claim 22 wherein an image rotator is arranged in the light path directed directly to the eyepiece from the objective between the one of said second reflectors made a reflector which can switch light paths and said fourth reflector.

24. An optical system for retinal cameras according to claim 22 further comprising a dark tube arranged between said first reflector and fourth reflector.

25. An optical system for retinal cameras according to claim 24 wherein said illuminating optical system is arranged in a zone enclosed with the light path bent by said second reflectors and the light path of the light reflected by said first reflector to be directed to said eyepiece.

26. An optical system for retinal cameras according to claim 22 further comprising a beam splitter provided between said first and fifth reflectors and a light receiving element arranged in the light path of the light divided by said beam splitter to receive it and thereby to generate a signal for effecting at least one of automatic focusing and automatic exposure controlling.

27. An optical system for retinal cameras according to claim 1 further comprising a light path bending third reflector which is provided between said first reflector and eyepiece, to bend the light path from said first reflector and then direct it to said eyepiece.

28. An optical system for retinal cameras comprising an objective for forming a retina image of an eye to be inspected, an illuminating optical system including therein a light source to illuminate the surface of the retina, a relay lens for leading to a film surface the retina image formed by said objective, a first reflector which can switch light paths and is arranged between said relay lens and the position of the retina image focused by said relay lens, an eyepiece arranged in the light path of the light reflected by said first reflector, characterized in that said optical system further comprises at least two light path bending second reflectors which are provided between said objective and relay lens, which bend the light path from the objective and then direct it to the relay lens, and a third reflector which can switch light paths and is arranged between said first reflector and the position of the retina image formed on said film surface by said relay lens so that a color film and a monochromatic film can be arranged in the positions of the retina image by said relay lens in the respective light paths swithced by said third reflector.

29. An optical system for retinal cameras according to claim 28 further comprising a light path bending fourth reflector which is provided between said first reflector and eyepiece, to bend the light path from said first reflector and then direct it to said eyepiece.

30. An optical system for retinal cameras comprising an objective for forming a retina image of an eye to be inspected, an illuminating optical system including therein a light source to illuminate the surface of the retina, a relay lens for leading to a film surface the retina image formed by said objective, a first reflector which can switch light paths and is arranged between said relay lens and the position of the retina image focused by said relay lens, an eyepiece arranged in the light path of the light reflected by said first reflector, characterized in that said optical system further comprises at least two light path bending second reflectors which are provided between said objective and relay lens, which bend the light path from the objective and then direct it to the relay lens, a third reflector which can switch light paths and is arranged between said first reflector and the position of the retina image formed on said film surface by said relay lens so that a color film and monochromatic film can be arranged in the positions of the retina image by said relay lens in the respective light paths switched by said third reflector, and a fourth reflector which can switch light paths and is arranged between said first reflector and eyepiece, the one reflector arranged in the position nearest to the objective of said second reflectors being able to switch light paths, and whereby the light having passed through the objective is led directly to the eyepiece by switching said one of said second reflectors and said fourth reflector and thereby the front part of the eye to be inspected can be observed.

31. An optical system for retinal cameras according to claim 30 wherein an image rotator is arranged in the light path directed directly to the eyepiece from the objective between the one of said second reflectors made a reflector which can switch light paths and said fourth reflector.

32. An optical system for retinal cameras according to claim 31 wherein auxiliary lenses for adjusting the magnification of the pupil and the position of the image are arranged near said image rotator.

33. An optical system for retinal cameras according to claim 30 further comprising a dark tube arranged between said first reflector and fourth reflector.

34. An optical system for retinal cameras according to claim 33 wherein said illuminating optical system comprises a fifth reflector having an aperture in the center and arranged between said objective and relay lens, a ring slit and a projecting lens for forming the image of said ring slit near said fifth reflector so that the illuminating light having passed through said ring slit is focused by said projecting lens and is then refocused near the cornea of the inspected eye by said objective.

35. An optical system for retinal cameras according to claim 33 wherein said illuminating optical system is arranged in an area enclosed with the light path bent by said second reflectors and the light path of the light reflected by said first reflector to be directed to said eyepiece.

36. An optical system for retinal cameras according to claim 32 further comprising a beam splitter provided between said first and fourth reflectors and a light receiving element arranged in the light path of the light divided by said beam splitter to receive it and thereby to generate a signal for effecting at least one of automatic focusing and automatic exposure controlling.

* * * * *